(12) United States Patent
Borik et al.

(10) Patent No.: US 8,371,850 B2
(45) Date of Patent: Feb. 12, 2013

(54) DEVICE FOR FORMING A BONE BED FOR DENTAL IMPLANTS

(76) Inventors: Mikhail A. Borik, Moscow (RU);
Vladimir P. Voitsitskiy, Moscow (RU);
Maria A. Vishniakova, Moscow (RU);
Elena E. Lomonova, Moscow (RU);
Viacheslav V. Osiko, Moscow (RU); Lev V. Chilikin, Moscow (RU)

( * ) Notice: Subject to any disclaimer, the term of this patent is extended or adjusted under 35 U.S.C. 154(b) by 510 days.

(21) Appl. No.: 12/565,732

(22) Filed: Sep. 23, 2009

(65) Prior Publication Data

US 2010/0047738 A1  Feb. 25, 2010

Related U.S. Application Data

(63) Continuation-in-part of application No. 11/624,427, filed on Jan. 18, 2007, now abandoned.

(51) Int. Cl.
*A61C 3/02* (2006.01)
(52) U.S. Cl. ........................................ 433/165
(58) Field of Classification Search .......... 433/165–166, 433/172–176; 408/223–224, 230; 175/394; 606/80; 407/53, 54; 144/240, 241; D8/20, D8/45
See application file for complete search history.

(56) References Cited

U.S. PATENT DOCUMENTS

| | | | | |
|---|---|---|---|---|
| 4,863,383 A | * | 9/1989 | Grafelmann | 433/174 |
| 5,642,996 A | * | 7/1997 | Mochida et al. | 433/174 |
| 5,653,627 A | * | 8/1997 | Nishi et al. | 451/540 |
| 7,481,652 B2 | * | 1/2009 | Senia et al. | 433/102 |
| 2003/0049586 A1 | * | 3/2003 | Kumar | 433/165 |
| 2006/0008771 A1 | * | 1/2006 | Courvoisier | 433/165 |

* cited by examiner

*Primary Examiner* — Todd Manahan
*Assistant Examiner* — Matthew Nelson
(74) *Attorney, Agent, or Firm* — Michelle P. Nguyen; John T. Lucas

(57) ABSTRACT

A device for forming a bone bed for dental implants having a head composed of crystal of partially stabilized zirconium dioxide with a nanostructure having a crystallographic axis that coincides with the axis of the bone bed forming device. The head has cutting elements formed as a rotatable plate. The plate has two broad facets formed by circular arcs that are convex relative to the axis of bone bed forming device. Transition from one of the convex circular arc to another convex circular arc is smoothed by circular arcs that are concave relative to the axis of bone bed forming device. Grooves form first and second cutting members with narrow facets of the plate. The head has an end part shaped as a truncated sphere possessing a recess formed by two planes arranged at an angle of 90° relative to each other and passing through the truncated sphere center and two points belonging to two diagonally arranged plate ribs. A third cutting member is formed by the intersection of one of the above mentioned two planes and a spherical surface of one of the narrow plate facets of the end part of the head.

6 Claims, 2 Drawing Sheets

DEVICE FOR FORMING A BONE BED FOR DENTAL IMPLANTS

CROSS-REFERENCE TO A RELATED APPLICATION

The invention described and claimed hereinbelow is a continuation-in-part of U.S. patent application Ser. No. 11/624,427 filed Jan. 18, 2007 now abandoned, which claims priority to Russian Patent Application 2006102210 filed on Jan. 26, 2006. The Russian Patent Application, whose subject matter is incorporated herein by reference, provides the basis for a claim of priority of invention under 35 U.S.C. 119(a)-(d).

BACKGROUND OF THE INVENTION

The proposed invention relates to medicine, in particular to surgical dentistry, and can be used for forming a bone bed for the placement of an implant.

Cylindrical and conical dental bone mills, (RU 2,251,391), for forming a bone bed for the placement of an implant, which include a tail part and cutting parts, are known. The cutting part has cutting edges of a straight shape and depressions. The depressions form an angle 60-90° therebetween. As a result, bone chip accumulation takes place. The mills are composed of tool steel or stainless steel, as a rule, with a subsequent anticorrosion coating with a titanium nitrate, which is a pronounced allergen. However, the coating has low strength and is worn relatively quickly during the operation process (i.e., low tribological properties). With cyclical loads, rapid destruction of the anticorrosion coating takes place, as well as contamination of the surface of the implant bed due to the metal from which the mill is produced. This often leads to destruction of the osteointegration process and causes postoperative complications.

Another problem of bone bed forming dental instruments is their heating at high rotary speeds (up to 1000 rev/min), which can cause a risk of thermal burn of the bone tissues of a patient. In order to reduce the risk of the thermal burn, the drill disclosed in RU Patent No. 2,151,570, includes a cylindrical body having a tail part, a working part with chutes, and cutting edges, as well as, channels formed with variable diameter inside the cylindrical body. Analogous solutions to reduce the risk of the thermal burn are disclosed in U.S. Pat. Nos. 5,575,651, 5,261,818, and German Patent No. 2,331,023. The provision of a uniform and constant flow of cooling liquid, for example water, provides significant reduction of the possibility of thermal injury to the treated bone tissue.

A high speed of rotation of a bone drilling instrument can also cause uncontrolled removal of material, depending on the force applied to the head. The invention disclosed in RU Patent No. 2,019,151 is directed to increasing treatment safety and simplification of construction. The drill operates at a high rotary speed, at or greater than 800 rev/min, which is disadvantageous. The tool provides removal of material in a dosed manner, during a single revolution, by a value not more than a height of the extension of the cutting element above the support, which does not allow for deeper penetration. The head and neck parts are composed of metal, while the cutting element has a diamond coating. Another disadvantage of this instrument is due to insufficient reliability caused by the rapid wearing of the coating, which is the result of crumbling of the ultra-dispersed diamonds of the cutting element.

The closest technical solution to the present proposal is a bone mill for an implant in accordance with the U.S. Pat. No. 6,659,769, which contains a tail part, a connecting neck, and a head with cutting elements formed as a plate of rotation. This construction partially resolves the problem of overheating and provides a removal of a bone chip. The disadvantage of this bone mill is that in its construction there is no limiting element for controlled removal of bone tissue. In addition, during an operation, the conical or cylindrical shape of the mill results in constant contact of the mill with the treated bone, which risks the possibility of thermal burn of the bone tissue.

What is needed is a device for forming a bone bed for dental implants having increased strength and wear-resistance, controlled removal of bone tissue, reduced risk of thermal burn to the bone tissues, as well as, a bone bed forming device having a surface corresponding to the surface of the implant.

SUMMARY OF THE INVENTION

Accordingly, it is an object of the present invention to provide a device for forming a bone bed for a dental implant, which eliminates the disadvantages of the prior art and is a further improvement of the existing devices of this type.

In keeping with these objects and with others which will become apparent hereinafter, one feature of the present invention resides, briefly stated, in a device for forming a bone bed for dental implants, containing a tail part, a connecting neck, and a head with cutting elements formed as a revolution (i.e., rotatable) plate. The two broad facets of the plate have a vertical profile formed by circular arcs that are convex relative to the device axis and have radii that grow smaller in the direction of translational movement of the bone bed forming device (i.e., R2 max to R1 max). Transition from one convex arc to another is smoothed with circular arcs arranged concave with respect to the device axis. Grooves are formed along the convex circular arcs on opposite sides of each broad facet of the plate. The grooves form the first and second cutting member groups with the two narrow facets of the plate. The end part of the head is shaped as a truncated sphere possessing a recess formed by two planes arranged at an angle of 90° relative to each other and passing through the truncated sphere center and two points belonging to two diagonally arranged plate ribs (i.e., edges). A third cutting member is formed by the intersection of one of the above mentioned two planes and a spherical surface of the narrow plate facet of the end part of the head. The device head is fabricated from partially stabilized zirconium dioxide having its crystallographic axis coinciding with the device axis.

The subject matter of the present invention is a combination of new elements concerning the construction and material used to make the bone bed forming device, which provides achievement of the technical results. The technical result of the present proposal is to provide controlled removal of the bone tissue, to reduce the risk of thermal burn, to increase strength and wear-resistance, and to provide ideal abutment of the formed bone bed to the implant used.

In particular, the proposed configuration of the rotary plate with the cutting members provides synchronous movement of bone chips with each cutting member, while the spherical shape of the surface of the narrow facets of the plate prevent uncontrolled penetration into the bone tissue and provide gaps between the bone tissue along the surface of the bone bed forming device during reduction of the radii of the convex circular arcs in the direction of translational movement of the bone bed forming device (i.e., R2 max to R1 max). Reduction of the risk of thermal burn of the bone tissue is provided by a significant reduction of the speed of rotation of the bone bed forming device, in particular around 200 revolutions per minute, and by the presence of gaps between the bone tissue along the surface of the bone bed forming device during reduction of the radii of the convex circular arcs in the direction of translational movement of the bone bed forming device (i.e., R2 max to R1 max). All of this combined provides for controlled removal of bone tissue, removal of bone chips, and reduces overheating of the bone tissue. Making the head from a high-strength wear-resistant material, (i.e., a crystal of partially stabilized zirconium dioxide) (PCZ), with a nanostructure having a crystallographic axis that coincides with the axis of the bone bed forming device, allows the device to cut at low rotary speeds without diminishing the cutting quality, which reduces the risk of thermal burn to the bone tissues. In addition, the wear resistance of PCZ minimizes contamination in the bone tissue, resulting in increased osteointegration of the implant into the bone tissue.

Construction of the bone bed forming device for the implant in accordance with the application of the same applicant 2005102197, RU Patent No. 2,284,790, is achieved by selection of an initial transverse size of the rotary plate that corresponds to the size of the implant used. The implant disclosed in the patent application of the same applicant no. 2005102197, RU Patent No. 2,284,790, is a perspective implant that can be used. The material of the implant, in accordance with the RU Patent No. 2,284,790, is a partially stabilized zirconium dioxide having a nanostructure, high strength, and wear resistance (i.e., high tribological properties).

The bone bed surface formed by the bone bed forming device is significantly congruent to the outside surface of the implant used. The absence of a gap between the formed bone bed surface and the implant allows osteointegration of the implant into the bone tissue. Thus, when the device is designed in accordance with the present invention, it has greater strength, it reduces risk of thermal burns to the bone tissues, and it provides considerable abutment of the implant against the bone bed.

The novel features which are considered characteristic for the present invention are set forth, in particular, in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

Figure 1:
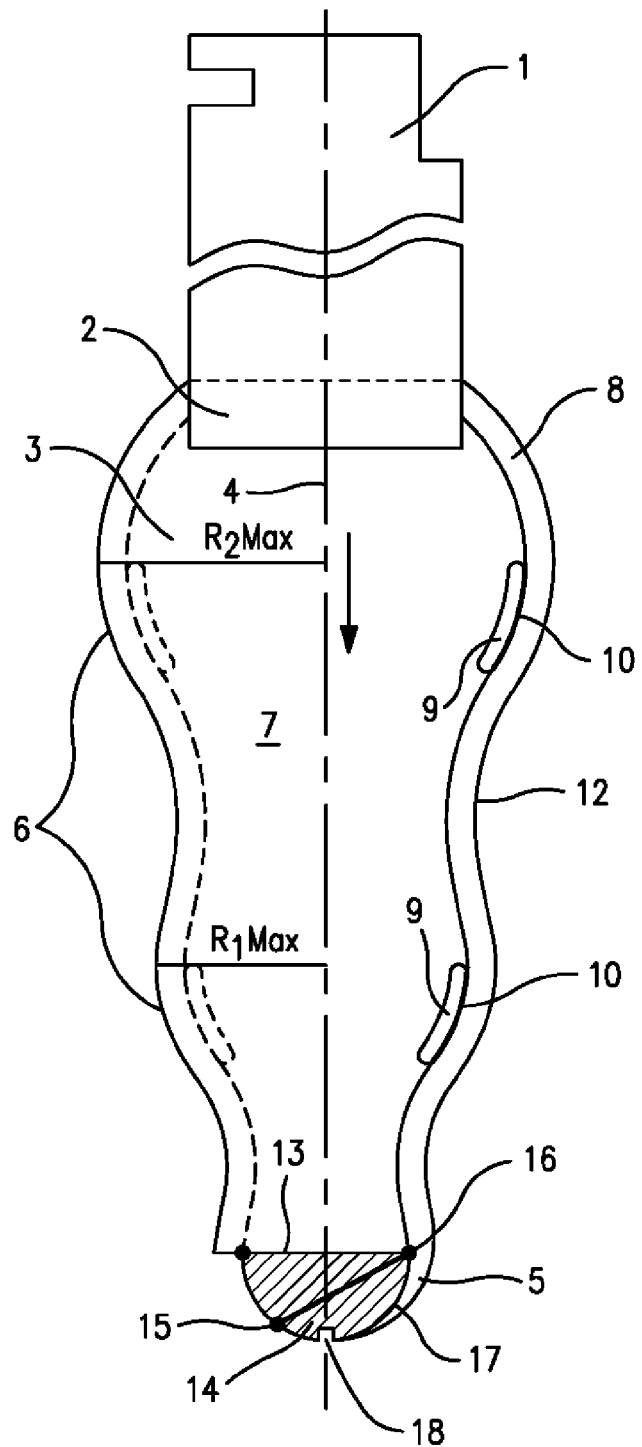
FIG. 1 is a front view schematically showing a device for forming a bone bed for a dental implant in accordance with the present invention.
Figure 2:
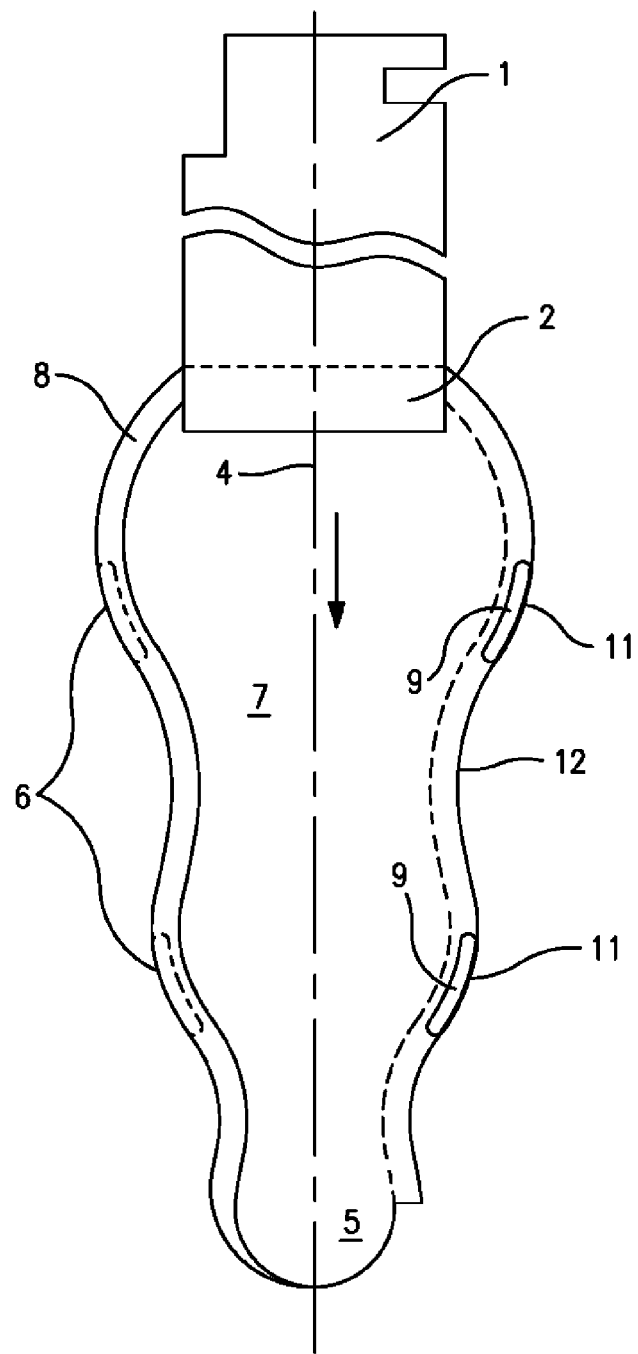
FIG. 2 is a rear view showing the device for forming a bone bed for a dental implant in accordance with the present invention.

The bone bed forming device has a tail part 1, a connecting neck 2, and a head 3 having cutting elements formed as a revolution (i.e., rotary) plate. The device has an axis which is identified with reference numeral 4. The device further has arcs 6 of circumferences that are convex relative to the axis of the device, arcs 12 of circumferences which are concave relative to the axis of the device, broad plate facets 7, narrow plate facets 8, and grooves 9, which are formed along the convex circular arcs 6 on opposite sides of each broad plate facet 7. The grooves form first and second cutting member groups, 10 and 11, respectively, with the two narrow plate facets 8. A sharpening angle is formed between the narrow plate facet 8 and a tangent to the circumference of the groove 9. The grooves can be formed along a direction of rotational movement of the plate from the beginning of the convex arcs 6 until they reach a maximum horizontal chord of the corresponding circumference (i.e., R1 max to R2 max in FIG. 1).

The end part of the head 5 is shaped as a truncated sphere possessing a recess 18 formed by two planes 13 and 14 arranged at an angle of 90° relative to each other and passing through the truncated sphere center and two points 15 and 16 belonging to two diagonally arranged plate ribs (i.e., edges). A third cutting element 17 is formed by the intersection of plane 14 and a spherical surface of the narrow plate facet 8 of the end part of the head 5. The tail part 1 and the connecting neck 2 can be composed of tool steel and are formed as a standard tail part of a dental drill. The head 3 is a one-piece structure and composed of a crystal PCZ with a nanostructure.

The bone bed forming device operates in the following manner. First, a guide channel is formed for a length of the implant to be used. Initial drilling of the bone tissue is carried out by a drill composed of tool steel. In order to minimize contamination (i.e., spreading infections), zirconium oxide is applied on the surface of the drill. The diameter of the drill is selected to be equal to the diameter of the sphere of the end part of the head of the device, which in turn is equal to the diameter of the semi-sphere of the apical end of the implant. In the formed channel, the end part of the head of the bone bed forming device is introduced. During rotation of the plate, first the cutting elements of the head with the smaller diameter operate, and during the advanced movement of the plate along the channel, the cutting elements of the first and second groups 10 and 11 operate. When the head reaches the bottom of the channel, the third cutting element 17 of the end part of the head starts working. The bone bed is formed this way so that its surface coincides with the surface of the implant, and therefore the process of installation of the implant is facilitated.

The proposed bone bed forming device has higher strength due to the use of the material coincidence of the crystallographic axis of the partially stabilized zirconium dioxide with the axis of the device. The proposed device also has a lower risk of thermal burns to the bone tissues due to operation at low speeds, in particular around 200 revolutions per minute. Furthermore, the proposed device has a simplified discharge of bone chips, due to the fact that, during rotation, the plate forms a stepped cylinder that includes cavities, wherein the discharge of bone chips is facilitated.sa It will be understood that each of the elements described above, or two or more together, may also find a useful application in other types of constructions differing from the type described above.

While the invention has been illustrated and described as embodied in a device for forming a bone bed for dental implants, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

The invention claimed is:

1. A device for forming a bone bed for a dental implant, comprising a bone bed forming element wherein a bone bed surface is formed by the bone bed forming element is congruent to an outside surface of the implant, without gaps between the formed bone bed surface and the implant, to allow for osteointegration of the implant into bone tissue, said forming element having a tail part for engagement with a rotatable drive, a connecting neck, and a head with cutting elements formed as a rotatable plate, said head being composed of a crystal of partially stabilized zirconium dioxide with a nanostructure and a crystallographic axis coinciding with an axis of said forming element, said plate having two broad facets, each facet with a vertical profile formed by at least two arcs that are convex relative to said axis of said forming element, with an entire transition from one of said convex arcs to another of said convex arcs being smoothed by arcs that are concave relative to said axis of said forming element, with grooves provided only along said convex arcs on opposite sides of each of said broad facets and forming with narrow facets of said plate a first group and a second group of cutting elements.

2. A device for forming a bone bed for dental implants as defined in claim 1, wherein said convex arcs have radii that grow smaller in the direction distal to the tail part.

3. A device for forming a bone bed for dental implants as defined in claim 1, wherein the device operates at a speed of about 200 revolutions per minute to reduce the risk of thermal burn to bone tissues.

4. A device for forming a bone bed for dental implants as defined in claim 1, wherein in use said plate forms the bone bed surface as a stepped cylinder that includes cavities to facilitate discharge of bone chips.

5. A device for forming a bone bed for dental implants as defined in claim 1, wherein said narrow facets of the plate prevent uncontrolled penetration into bone tissue.

6. A device for forming a bone bed for dental implants as defined in claim 1, wherein said head is made from a high-strength wear-resistant material.

* * * * *